(12) United States Patent
Maskara et al.

(10) Patent No.: US 8,577,456 B2
(45) Date of Patent: Nov. 5, 2013

(54) MEASURING AUTONOMIC TONE USING ATRIOVENTRICULAR DELAY

(75) Inventors: Barun Maskara, Blaine, MN (US);
Robert Shipley, Austin, TX (US);
Stephen Ruble, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 486 days.

(21) Appl. No.: 12/787,031

(22) Filed: May 25, 2010

(65) Prior Publication Data
US 2010/0305651 A1 Dec. 2, 2010

Related U.S. Application Data (60) Provisional application No. 61/181,576, filed on May 27, 2009.

(51) Int. Cl.
*A61B 5/0205* (2006.01)

(52) U.S. Cl.
USPC .................................. 607/17; 607/23; 607/27

(58) Field of Classification Search
USPC .................................................. 607/17, 23, 27
See application file for complete search history.

(56) References Cited

U.S. PATENT DOCUMENTS

2004/0215262 A1* 10/2004 Ferek-Petric .................. 607/17
2005/0055060 A1   3/2005 Koh et al.
2007/0055317 A1*  3/2007 Stahmann et al. ............. 607/23

* cited by examiner

*Primary Examiner* — Joseph Stoklosa
*Assistant Examiner* — Michael D Abreu
(74) *Attorney, Agent, or Firm* — Schwegman Lundberg & Woessner, P.A.

(57) ABSTRACT

An autonomic status indicator representative of a sympathetic/parasympathetic balance of a subject can use atrioventricular (AV) delays measured during recovery from (or in response to) elevated atrial pacing while the subject is at rest.

20 Claims, 5 Drawing Sheets

MEASURING AUTONOMIC TONE USING ATRIOVENTRICULAR DELAY

CROSS-REFERENCE TO RELATED APPLICATION

This application claims the benefit of U.S. Provisional Application No. 61/181,576, filed on May 27, 2009, under 35 U.S.C. §119(e), which is hereby incorporated by reference in its entirety.

BACKGROUND

Autonomic tone can be an important diagnostic and therapeutic indicator in the management of cardiac disease.

OVERVIEW

This document describes, among other things, a system and method of determining an autonomic status indicator representative of a sympathetic/parasympathetic balance of a subject by using atrioventricular (AV) delays measured during recovery from (or in response to) elevated atrial pacing while a subject is at rest.

Example 1 can include subject matter that can include a system comprising: a cardiac rhythm management device, the cardiac rhythm management device comprising: an atrial pacing circuit, configured to provide, during a testing time period, atrial pacing to a subject at rest, over a specified range of atrial pacing rates or intervals; and an intrinsic AV delay measurement circuit, configured to: measure, during the testing time period, intrinsic AV delays of the subject, over the specified range of atrial pacing rates or intervals; determine a baseline intrinsic AV delay of the subject at rest during a time other than the testing time period; and in response to and after the atrial pacing is terminated, measure intrinsic AV delays of the subject during a recovery time period; and a processor, included in or coupled to the cardiac rhythm management device, the processor configured to use information about a duration of the recovery time period to determine a first autonomic status indicator representative of a sympathetic/parasympathetic balance of the subject.

In Example 2, the subject matter of Example 1 can optionally include the recovery time period ending when the subject's measured AV delay is approximately equal to the baseline intrinsic AV delay.

In Example 3, the subject matter of any one of Examples 1-2 can optionally include the cardiac rhythm management device configured to provide atrial pacing, during the testing time period, at a rate that is above the subject's intrinsic resting heart rate.

In Example 4, the subject matter of any one of Examples 1-3 can optionally include a user interface, coupled to the processor to receive information about the first autonomic status indicator, and to provide information about the first autonomic status indicator to a user or automated process.

In Example 5, the subject matter of any one of Examples 1-4 can optionally include the processor configured to use the first autonomic status indicator to adjust a therapy provided to the subject by a medical device.

In Example 6, the subject matter of any one of Examples 1-5 can optionally include the therapy including a neurostimulation therapy.

In Example 7, the subject matter of any one of Examples 1-6 can optionally include the processor configured to: determine a slope or rate of change characteristic of the relationship, each data pair representing (1) the measured intrinsic AV delay and (2) corresponding atrial pacing rate or interval at which the AV delay was measured; and use information about the slope or rate of change characteristic for providing a second autonomic status indicator representative of a sympathetic/parasympathetic balance of the subject.

In Example 8, the subject matter of any one of Examples 1-7 can optionally include the processor configured to determine, for a data pair, a central tendency of multiple measured intrinsic AV delays associated with the same corresponding atrial pacing rate or interval.

In Example 9, the subject matter of any one of Examples 1-8 can optionally include the processor configured to compare the slope or rate of change characteristic of the relationship to a threshold value and use a result of the comparison for providing the second autonomic status indicator representative of a sympathetic/parasympathetic balance of the subject.

In Example 10, the subject matter of any one of Examples 1-9 can optionally include a user interface, configured to be coupled to the processor to receive information about the second autonomic status indicator, and to provide information about the second autonomic status indicator to a user or automated process.

In Example 11, the subject matter of any one of Examples 1-10 can optionally include the processor configured to combine information about the first and second autonomic status indicators, and wherein the user interface is configured to provide information about both the first and second autonomic status indicators to the user or automated process.

In Example 12, the subject matter of any one of Examples 1-11 can optionally include the processor configured to use the first and second autonomic status indicators to adjust a therapy provided to the subject by the cardiac rhythm management device.

Example 13 can include, or can optionally be combined with any one of Examples 1-12 to include subject matter that can include: during a testing time period, using a cardiac rhythm management device for providing atrial pacing to a subject at rest, over a specified range of atrial pacing rates or intervals; during the testing time period, using the cardiac rhythm management device for measuring intrinsic AV delays of the subject, over the specified range of atrial pacing rates or intervals; determining a baseline intrinsic AV delay of the subject at rest during a time other than the testing time period; in response to and after the atrial pacing is terminated, using the cardiac rhythm management device for measuring intrinsic AV delays of the subject during a recovery time period; using information about a duration of the recovery time period to determine, using a processor, a first autonomic status indicator representative of a sympathetic/parasympathetic balance of the subject; and providing information about the second autonomic status indicator to the user or automated process.

In Example 14, the subject matter of any one of Examples 1-13 can optionally include the recovery time period ending when the subject's measured AV delay is approximately equal to the baseline intrinsic AV delay.

In Example 15, the subject matter of any one of Examples 1-14 can optionally include providing atrial pacing at a rate that is above the subject's intrinsic resting heart rate.

In Example 16, the subject matter of any one of Examples 1-15 can optionally include using the first autonomic status indicator to adjust a therapy provided to the subject by the cardiac rhythm management device.

In Example 17, the subject matter of any one of Examples 1-16 can optionally include using information about a relationship between (1) the measured intrinsic AV delays and (2) the provided atrial pacing rates or intervals, to determine, using a processor, a second autonomic status indicator representative of a sympathetic/parasympathetic balance of the subject; and providing information about the second autonomic status indicator to a user or automated process.

In Example 18, the subject matter of any one of Examples 1-17 can optionally include forming data pairs, each data pair representing (1) the measured intrinsic AV delay and (2) corresponding atrial pacing rate or interval at which the AV delay was measured; defining the relationship between (1) the measured intrinsic AV delays and (2) the provided atrial pacing rates or intervals using the data pairs; determining a slope or rate of change characteristic of the relationship; and using information about the slope or rate of change characteristic for providing the second autonomic status indicator representative of a sympathetic/parasympathetic balance of the subject.

In Example 19, the subject matter of any one of Examples 1-18 can optionally include determining, for a data pair, a central tendency of multiple measured intrinsic AV delays associated with the same corresponding atrial pacing rate or interval.

In Example 20, the subject matter of any one of Examples 1-19 can optionally include comparing the slope or rate of change characteristic of the relationship to a threshold value, and using a result of the comparing for providing the second autonomic status indicator representative of a sympathetic/parasympathetic balance of the subject.

In Example 21, the subject matter of any one of Examples 1-20 can optionally include combining information about the first and second autonomic status indicators, and comprising providing information about both the first and second autonomic status indicators to the user or automated process.

In Example 22, the subject matter of any one of Examples 1-21 can optionally include using the first and second autonomic status indicators to adjust a therapy provided to the subject by a medical device.

In Example 23, the subject matter of any one of Examples 1-22 can optionally include the therapy including a neurostimulation therapy.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document describes, among other things, a system and method for determining an autonomic status indicator representative of sympathetic/parasympathetic balance of a subject. Such an autonomic status indicator can be used to evaluate the status of the subject's autonomic nervous system or to adjust therapy provided to the subject.

Cardiac function is controlled, in part, by the autonomic nervous system, which includes the sympathetic nervous system and the parasympathetic nervous system. The sympathetic nervous system is associated with stress and the "fight or flight response" to emergencies. Among other effects, the "fight or flight response" increases heart rate and blood pressure to increase skeletal muscle blood flow. The parasympathetic nervous system is associated with relaxation and the "rest and digest response" which, among other effects, decreases heart rate and blood pressure, and increases digestion to conserve energy. The sympathetic and parasympathetic nervous systems continually work in tandem to achieve homeostasis.

In a normal subject, increased activity of the sympathetic nervous system (or decreased activity of the parasympathetic nervous system), referred to as an increase in sympathetic tone, can occur, for example, in response to exercise. During exercise, increased sympathetic tone causes an increase in heart rate. Increased sympathetic tone also results in a shortened atrioventricular (AV) delay. This allows the heart to pump more blood at a faster rate in order to meet the body's increased metabolic needs during exercise. In contrast, increased activity of the parasympathetic nervous system (or decreased activity of the sympathetic nervous system), referred to as an increase in parasympathetic tone, can occur, for example, when the subject stops exercise and is at rest. While at rest, increased parasympathetic tone causes a decrease in heart rate. Increased parasympathetic tone also results in a longer AV delay. This allows the heart to pump less blood at a slower rate in order to conserve energy during times of decreased metabolic demand.

With the use of a pacer or other cardiac function management system, heart rate can be artificially increased, for example, (such as in a patient without blockage of intrinsic heart signals at the atrioventricular node) by increasing the atrial pacing rate while a subject is at rest. When the atrial pacing rate in a normal subject at rest is artificially increased, the subject's AV delay will lengthen. In this situation, the subject does not have an increased metabolic demand (since the patient is at rest), yet the heart is pumping blood at an increased rate. In order to counteract the artificially high atrial pacing rate, the subject's parasympathetic tone will increase, resulting in a lengthened AV delay. In subjects with an autonomic nervous system imbalance, however, it is believed that the normal AV delay response to an artificially increased atrial pacing rate can either be blunted or overly strong. For example, if a subject's parasympathetic tone is abnormally low, the subject's AV delay may not lengthen appropriately in response to an artificial increase in atrial pacing for a resting subject. On the other hand, if a subject's parasympathetic system is in overdrive, which could be caused for example by a drug such as a beta-blocker, the subject's AV delay may increase too much in response to an artificial increase in atrial pacing for a resting subject.

Figure 1:
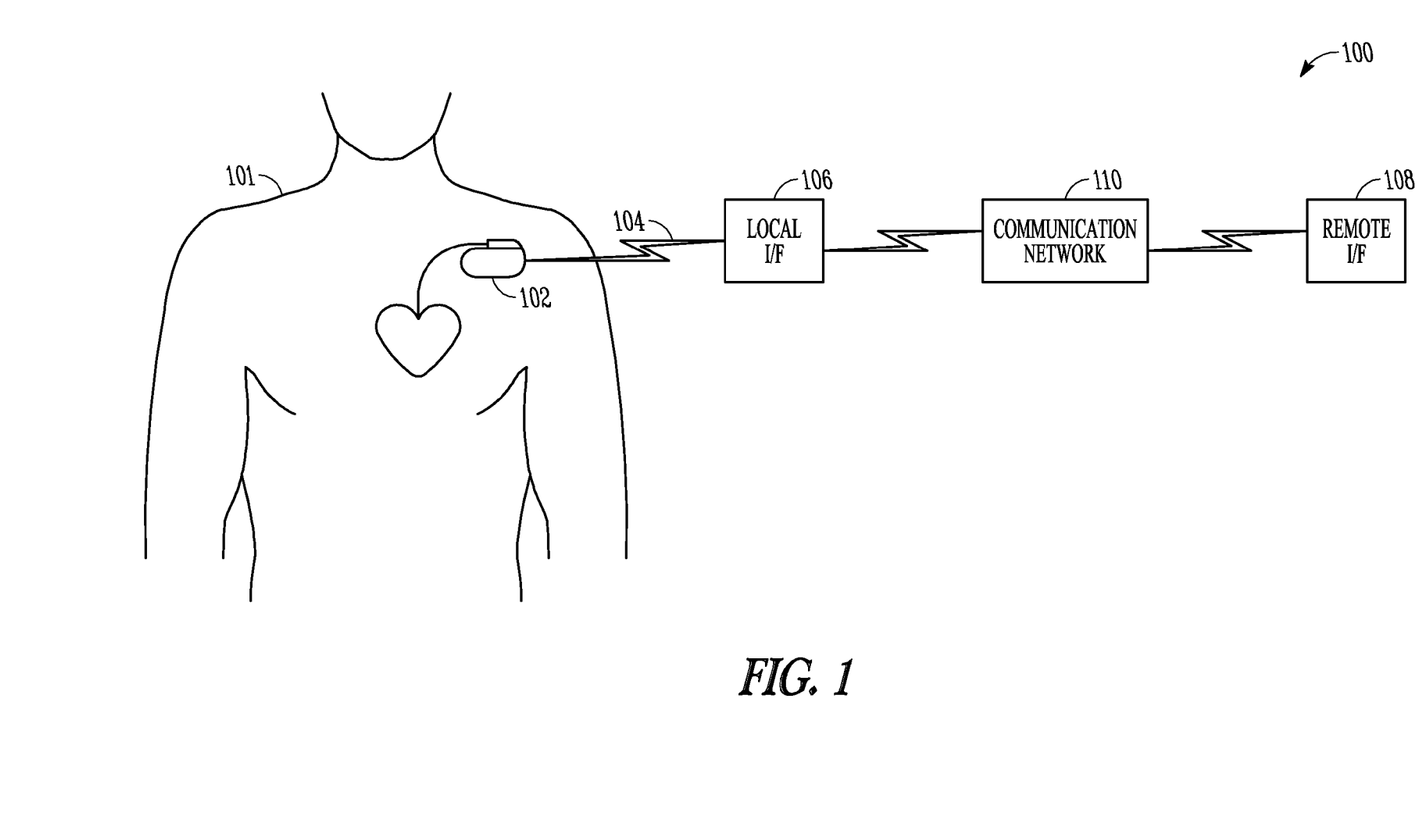
FIG. 1 is schematic diagram illustrating generally an example of a cardiac function management system, such as for use with a human or animal subject.

Recognizing this, the present inventors have further recognized that a measure of a subject's AV delay response, such as to an artificial increase in atrial pacing (e.g., for a resting subject) can be used as a measure of the subject's autonomic condition. Moreover, it is believed that measuring autonomic condition while a subject is at rest (by artificially increasing atrial pacing), as opposed to conducting an exercise test, can be beneficial because it can be easier for the subject, it can be less time consuming and less expensive, it can be performed in a variety of settings and even at home, and it can be done more frequently, such as on a weekly basis. FIG. 1 is schematic diagram illustrating generally an example of a cardiac function management system 100, such as for use with a human or other living subject 101. In this example, the system 100 can include an implantable or external cardiac function management (CFM) device 102. Examples of CFM device 102 can include, without limitation, a pacemaker, a cardioverter, a defibrillator, a cardiac resynchronization therapy (CRT) device, or other cardiac monitoring or therapy delivery device, for example, including a cardiac device that includes or works in coordination with one or more neuro-stimulating devices, or other devices, drugs, drug delivery systems, or other therapies. The CFM device 102 can include a communication circuit, such as for establishing a unidirectional or bidirectional wireless communication link 104 with an external local interface 106, with an implantable or external posture sensor, or with other device with communication capability. In an example, the external local interface 106 can further unidirectionally or bidirectionally communicate with an external remote interface 108, such as wirelessly or otherwise, such as via a shared communication or computer network 110.

Figure 2:
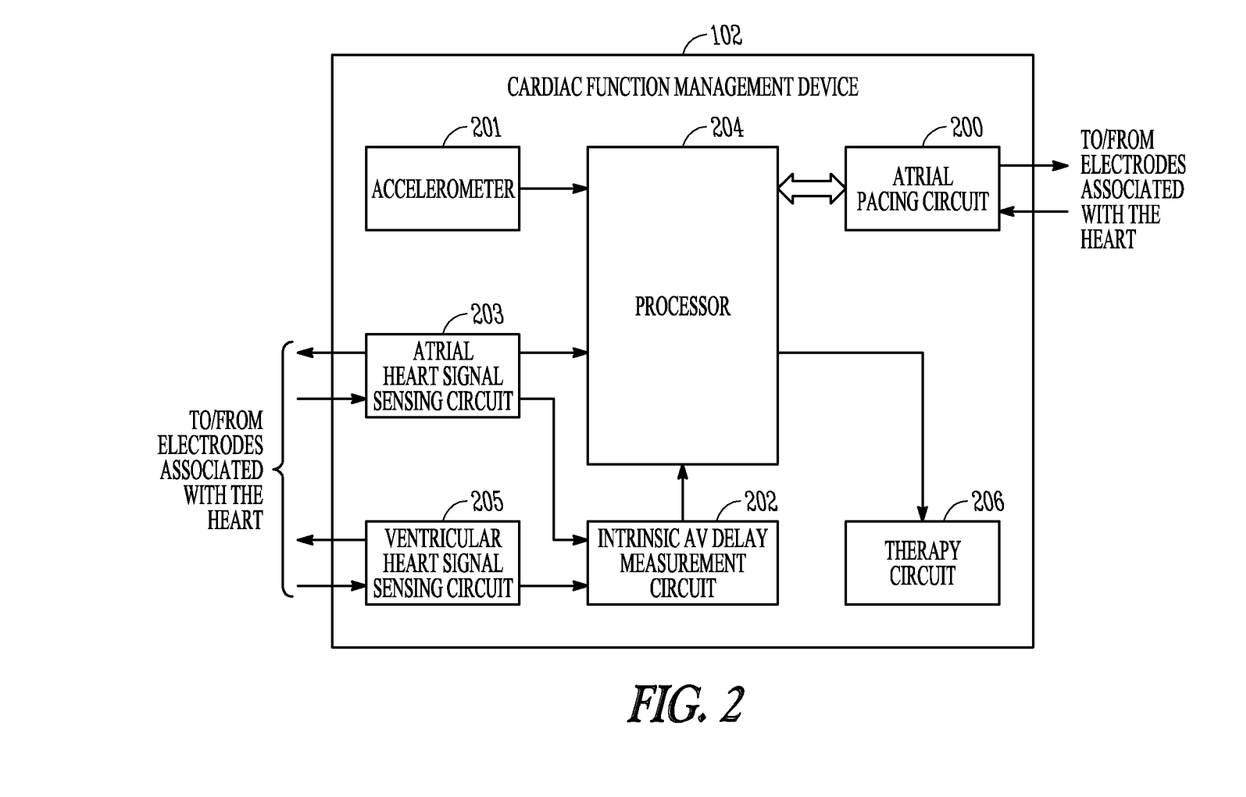
FIG. 2 is a block diagram illustrating generally an example of a system for determining an autonomic status indicator representative of sympathetic/parasympathetic balance of a subject.

FIG. 2 is a block diagram further illustrating an example of a CFM device 102, such as for use in determining an autonomic status indicator representative of sympathetic/parasympathetic balance of a subject. The CFM device 102 can include an atrial pacing circuit 200, which can be configured to provide atrial pacing to a subject at rest. An accelerometer 201, or any other sensor of physical activity or exertion, can be used to determine when the subject is at rest. In this example, the accelerometer 201 is coupled to a processor 204, which, in turn, is coupled to the atrial pacing circuit 200. Information from the accelerometer 201 can be communicated to the processor 204, and the processor 204 can then control the atrial pacing provided by the atrial pacing circuit 200. For example, when the accelerometer 201 indicates that the subject is at rest, the processor 204 can direct the atrial pacing circuit 200 to provide atrial pacing. On the other hand, when the accelerometer 201 indicates that the subject is not at rest, the processor 204 can inhibit the atrial pacing provided by the atrial pacing circuit 200.

The atrial pacing circuit 200 can provide atrial pacing during a testing time period, for example, while the subject is known or determined to be at rest. Furthermore, the atrial pacing circuit 200 can provide atrial pacing over a specified range of atrial pacing rates or intervals. The atrial pacing provided by the atrial pacing circuit 200 can be at a rate that is above the subject's intrinsic atrial heart rate. The subject's intrinsic atrial heart rate can be determined by an atrial heart signal sensing circuit 203, coupled to electrodes for sensing an atrial heart signal. The atrial heart signal sensing circuit 203 can also be coupled to the processor 204, which can be configured to extract the subject's intrinsic atrial heart rate from information provided by the atrial heart signal sensing circuit 203. The processor 204 can then use the extracted intrinsic atrial heart rate to control the atrial pacing circuit 200 such that the atrial pacing provided to the subject is at a rate that is above the subject's intrinsic atrial heart rate.

The CFM device 102 also includes an intrinsic AV delay measurement circuit 202, which can be configured to measure, during the testing time period, intrinsic AV delays of the subject, such as over the specified range of atrial pacing rates or intervals that are used during the testing time period. The intrinsic AV delay measurement circuit 202 can be configured to receive information from the atrial heart signal sensing circuit 203, and from a ventricular heart signal sensing circuit 205, which can be coupled to electrodes for sensing a ventricular heart signal. Using information from both the atrial heart signal sensing circuit 203 and the ventricular heart signal sensing circuit 205, the intrinsic AV delay measurement circuit 202 can determine the subject's intrinsic AV delay measurements.

The processor 204 can also be coupled to the intrinsic AV delay measurement circuit 202. In the example shown, the processor 204 is included within the CFM device 102. In other examples, the processor 204 can be a separate implantable or external device that can be communicatively coupled to CFM device 102. The processor 204 can be configured to use information about a relationship between the measured intrinsic AV delays over the specified range of the provided atrial pacing rates such as to determine a second autonomic status indicator representative of a sympathetic/parasympathetic balance of a subject (a first autonomic status indicator will be discussed below). The processor can be configured to use the second autonomic status indicator to control a therapy circuit 206, such as to adjust a therapy provided to the subject. The processor 204 can also be coupled to a local or remote external user interface capable of receiving information about the second autonomic status indicator and providing such information to a user or automated process. In addition, the processor 204 can be configured to interpret or execute software or other instructions that provide such an automated process, such as to control delivery of a cardiac function management therapy by the CFM device 102.

The processor 204 can be configured to collect data pairs representing (1) a measured intrinsic AV delay obtained from the intrinsic AV delay measurement circuit 202, and (2) the corresponding atrial pacing rate or interval at which the AV delay was measured. The corresponding atrial pacing rate or interval can be obtained from the processor 204, which can provide such atrial pacing rate control information to the atrial pacing circuit 200. The processor 204 can then use the data pairs, such as to determine a slope or rate of change characteristic of relationship such as can be observed in a plot of one component of the data pair against the other component of the data pair. Such a slope or rate of change characteristic, in turn, can be used to provide the second autonomic status indicator. The processor 204 can be configured to determine, for a given atrial pacing rate or interval, a central tendency of multiple corresponding measured intrinsic AV delays measured at that atrial pacing rate or interval. This information can be used to determine a data pair formed by (1) the central tendency of the measured AV delays and (2) the atrial pacing rate or interval. The processor 204 can also be configured to compare the slope or rate of change characteristic, such as to a threshold value, and to use a result of the comparison to provide the second autonomic status indicator.

Moreover, the processor 204 can be configured to use the second autonomic status indicator or one or more other autonomic status indicators to adjust a therapy provided to the subject, such as by the CFM device 102. Therapy adjustment can include, for example, titration of a medication.

The CFM device 102 or the processor 204 can be configured to perform a user-commanded test, such as in which a user can command the testing time period to begin. The user-commanded test can be triggered, for example, when a user presses a button located on a local or remote external user interface coupled to the CFM device 102. This can allow the user to obtain an on-demand indication of the subject's autonomic status, which can be useful, for example, in evaluating a subject's response to medication.

A recovery time of the AV delay can also provide an indication of autonomic status. For example, during the testing time interval, the intrinsic AV delay measurement circuit 202 can be configured to first determine an initial baseline intrinsic AV delay of the subject at rest. Then, atrial pacing circuit 200 can provide atrial pacing over a specified range of atrial pacing rates or intervals that is above the subject's intrinsic atrial heart rate, such as described above. Then, the atrial pacing can be discontinued, and after discontinuing the atrial pacing, the intrinsic AV delay measurement circuit 202 can be configured to measure intrinsic AV delays of the subject during a recovery time period portion of the testing time period. In an example, the recovery time period can be defined such that the recovery time period ends when the subject's measured AV delay returns to be approximately equal (e.g., within 10-15 milliseconds) to the previously-measured baseline intrinsic AV delay. The processor 204 can be configured to use information about the measured duration of the recovery time period, such as to determine a first autonomic status indicator representative of a sympathetic/parasympathetic balance of the subject. The processor 204 can be coupled to a user interface capable of receiving information about the first autonomic status indicator, and to provide such information to a user or automated process. Furthermore, the processor 204 can be configured to combine information about the first and second autonomic status indicators with each other or with another automatic status indicator (e.g., derived from heart rate variability (HRV), etc.), and such information can be provided to the user or an automated process, such as for closed-loop or other control of a cardiac function management therapy. For example, the processor 204 can be configured to use the first and second autonomic status indicators to adjust a therapy provided to the subject by the CFM device 102. Examples of such therapy adjustment can include, for example, titration of a medication, adjustment of cardiac resynchronization therapy (CRT), pacing therapy, or neurostimulation therapy, which can be provided by the same CFM device 102 or a separate implantable or external medical device.

In an example, neurostimulation therapy can be provided via an implantable nerve stimulation device, or using a non-implantable system such as can be configured for providing transcranial stimulation. Neurostimulation therapy can be used to treat one or more conditions associated with sympathetic/parasympathetic imbalance, such as heart failure, myocardial infarction, ventricular arrhythmias, syncope, sleep apnea, depression, epilepsy, movement disorders, erectile dysfunction, migraine headaches, and atherosclerosis, for example. Using information about the first and second autonomic indicators, neurostimulation therapy can be provided or modified, such as based on one or more of duty cycle, frequency, pulse width, amplitude, pattern of stimulation, waveform, polarity, electrode configuration, and location of stimulation, for example.

Figure 3:
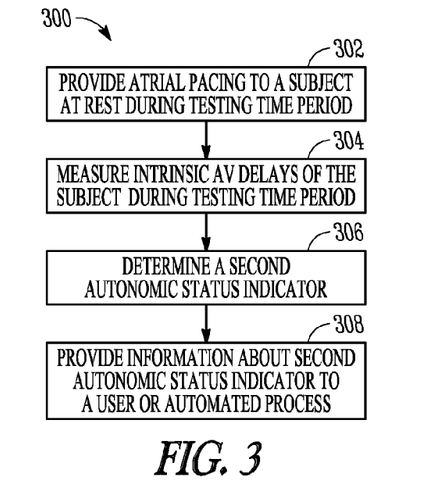
FIG. 3 is a chart illustrating an example of a method for determining an autonomic status indicator representative of sympathetic/parasympathetic balance of a subject.

FIG. 3 is a chart illustrating an example of a method 300, such as for determining an autonomic status indicator representative of sympathetic/parasympathetic balance of a subject. At 302, atrial pacing can be provided to a subject at rest. An accelerometer can be used to ensure that the subject is at rest or to accurately determine the subject's level of physical activity or exertion. An implantable or other CFM device can be used to provide the atrial pacing. The atrial pacing can be provided during a testing time period, such as over a specified range of atrial pacing rates or intervals. For example, the atrial pacing can start at a rate that is 10 beats per minute (bpm) (or other specified amount) above a subject's intrinsic atrial heart rate, such as can be measured using an atrial intrinsic heart signal sensing circuit of the CFM device. After being paced for 30 seconds at 10 bpm above the subject's intrinsic atrial heart rate, the atrium can then be paced for the next 30 seconds at 20 bpm above the subject's intrinsic atrial heart rate, and then for the next 30 seconds at 30 bpm above the subject's intrinsic atrial heart rate, and so on, up to a specified atrial upper pacing rate limit. In other words, the atrium can be paced at each specified rate for a specified period (e.g., 30 seconds), and the rate can be increased by 10 bpm every 30 seconds.

At 304, intrinsic AV delays of the subject can be measured, such as by using the CFM device. The intrinsic AV delays of the subject can be measured during the same testing time period during which the atrial pacing is provided, such that the measured AV delays are measured over the same specified range of atrial pacing rates or intervals. For example, the AV delay measurements can be conducted during the last 10 seconds of each 30-second pacing interval described above. Measuring the AV delay during the last 10 seconds of each 30-second pacing interval can allow the atrial pacing interval to reach a steady state before the AV delay measurements are taken.

Data pairs can be formed using the intrinsic AV delay measured at 304 and the corresponding atrial pacing rate or interval provided concurrently thereto at 302. Each data pair represents (1) a measured intrinsic AV delay, and (2) the corresponding atrial pacing rate or interval at which the AV delay was measured. Data pairs can be formed, for example, by determining, for a data pair, a central tendency of multiple measured intrinsic AV delays associated with the same corresponding atrial pacing rate or interval. In an example, the data pairs can then be used to define a relationship between (1) the measured intrinsic AV delays, and (2) the provided atrial pacing rates or intervals. Once such a relationship has been defined, a slope or rate of change characteristic of the relationship can be determined. Compared to the slope or rate of change characteristic of a healthy subject, a steeper slope or rate of change characteristic can be indicative of increased parasympathetic tone. On the other hand, compared to the slope or rate of change characteristic of a healthy subject, a shallower slope or rate of change characteristic can be indicative of decreased parasympathetic tone. These examples will be explored in greater detail below with respect to FIGS. 6-8.

At 306, a second autonomic status indicator representative of a sympathetic/parasympathetic balance of the subject is determined. The second autonomic status indicator can be determined, for example, by using information about the relationship between (1) the measured intrinsic AV delays, and (2) the provided atrial pacing rates or intervals, including the slope or rate of change characteristic of the relationship. The slope or rate of change characteristic of the relationship can be used to provide the second autonomic indicator. In addition, the slope or rate of change characteristic of the relationship can optionally be compared to a threshold value, and the results of the comparison can be used to provide the second autonomic indicator. The threshold value can be determined, for example, by calculating a central tendency of the slopes or rate of change characteristics obtained from a plurality of test subjects in a population-based study.

At 308, information about the second autonomic status indicator can be provided to a user or automated process. Providing the second autonomic status indicator can include using the second autonomic indicator to adjust a therapy provided to the subject by the CFM device. Adjusting therapy can include titrating a drug or medicine, such as a beta-blocker or AV nodal blocking drug. Other examples of therapies that can be adjusted in response to an autonomic indicator include, without limitation, cardiac resynchronization therapy, atrial or ventricular pacing therapy, atrial or ventricular anti-tachyarrhythmia therapy, and atrial or ventricular multi-site coordination therapy, such as biventricular pacing or univentricular multi-site pacing.

Figure 4:
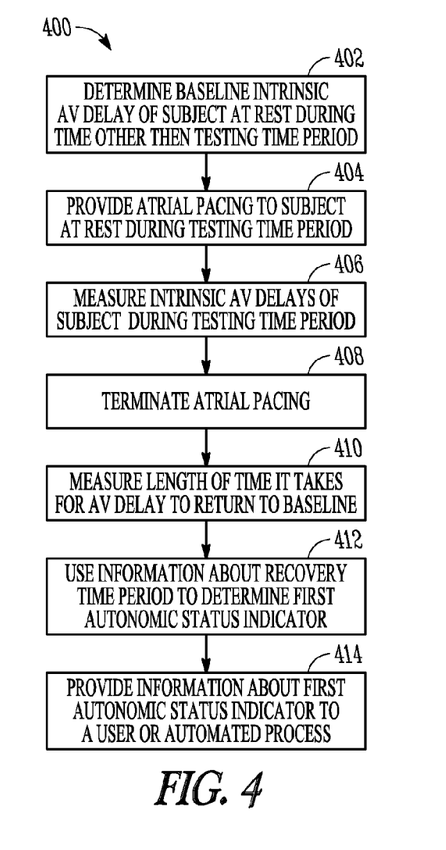
FIG. 4 is a chart illustrating another example of a method for determining an autonomic status indicator representative of sympathetic/parasympathetic balance of a subject.

FIG. 4 is a chart illustrating an example of a method 400 for determining an autonomic status indicator representative of sympathetic/parasympathetic balance of a subject. At 402, a baseline intrinsic AV delay of a subject at rest can be determined, such as during an initial portion of the testing time period before atrial pacing at rates higher than the intrinsic atrial rate is initiated. The baseline intrinsic AV delay is determined when the subject can be at rest. The baseline intrinsic AV delay can be determined, for example, by measuring a plurality of intrinsic AV delays of the subject at rest during a time period without providing the atrial pacing, and then calculating a central tendency value representative of the baseline intrinsic AV delay.

At 404, atrial pacing can be provided to the subject at rest during the testing time period. A CFM device can be used to provide the atrial pacing. The atrial pacing can be provided over a specified range of atrial pacing rates or intervals. For example, the atrial pacing can start at a rate that is 10 beats per minute (bpm) (or other specified rate) above a subject's intrinsic atrial heart rate. After being paced for 30 seconds (or other specified time) at 10 bpm above the subject's intrinsic atrial heart rate, the atrium can then be paced for the next 30 seconds at 20 bpm above the subject's intrinsic rate, and then for the next 30 seconds at 30 bpm above the subject's intrinsic rate, and so on, up to a specified atrial upper pacing rate limit. In other words, the atrium can be paced at each rate for 30 seconds, and the rate can be increased by 10 bpm every 30 seconds. At 406, corresponding intrinsic AV delays of the subject are measured using the CFM device. The intrinsic AV delays of the subject can be measured during the same testing time period in which the atrial pacing is provided, and in response thereto, and over the same specified range of atrial pacing rates or intervals. For example, the AV delay measurements can be conducted during the last 10 seconds of each 30-second pacing interval described above.

At 408, the atrial pacing can be discontinued. In response to and after the atrial pacing is discontinued, the CFM device can be used to measure intrinsic AV delays of the subject during a recovery time period. The CFM device can continue to measure the subject's intrinsic AV delays until the subject's AV delay is approximately equal to (or within a specified margin of) the baseline intrinsic AV delay, at which point the recovery time period ends. In an example, the recovery time period ends and the CFM ceases to measure intrinsic AV delays when the subject's measured intrinsic AV delay is within 10-15 milliseconds of the baseline intrinsic AV delay.

At 410, the length of time it takes for the intrinsic AV delay to return to baseline (e.g., the duration of the recovery period) is measured. At 412, this measured length of time, which can be referred to as the recovery period duration, can be used to determine a first autonomic status indicator representative of a sympathetic/parasympathetic balance of the subject. The recovery time period can be used to provide the first autonomic indicator. In addition, the recovery time period can optionally be compared to a threshold value, and the results of the comparison can be used to provide the first autonomic indicator. The threshold value can be determined, for example, by calculating a central tendency of the recovery time period for a plurality of test subjects in a population-based study. If, for example, the recovery time period is much longer than the threshold value, the subject may have an abnormally low parasympathetic tone, which could be due to a medication such as a beta-blocker. In this case, the first autonomic indicator would reflect a low parasympathetic tone.

At 414, information about the first autonomic status indicator can be provided to a user or automated process. In an example, information about the second autonomic indicator, obtained according to method 300, and information about the first autonomic status indicator, obtained according to method 400, can be combined with each other or with another autonomic indicator (e.g., heart rate variability) and provided to the user or automated process. Combined information about the first and second (or other) autonomic status indicators can also be used to adjust a therapy provided to the subject by the CFM device. Adjusting a therapy can include titrating a drug or medication, such as a beta-blocker or an AV nodal blocking drug.

Figure 5:
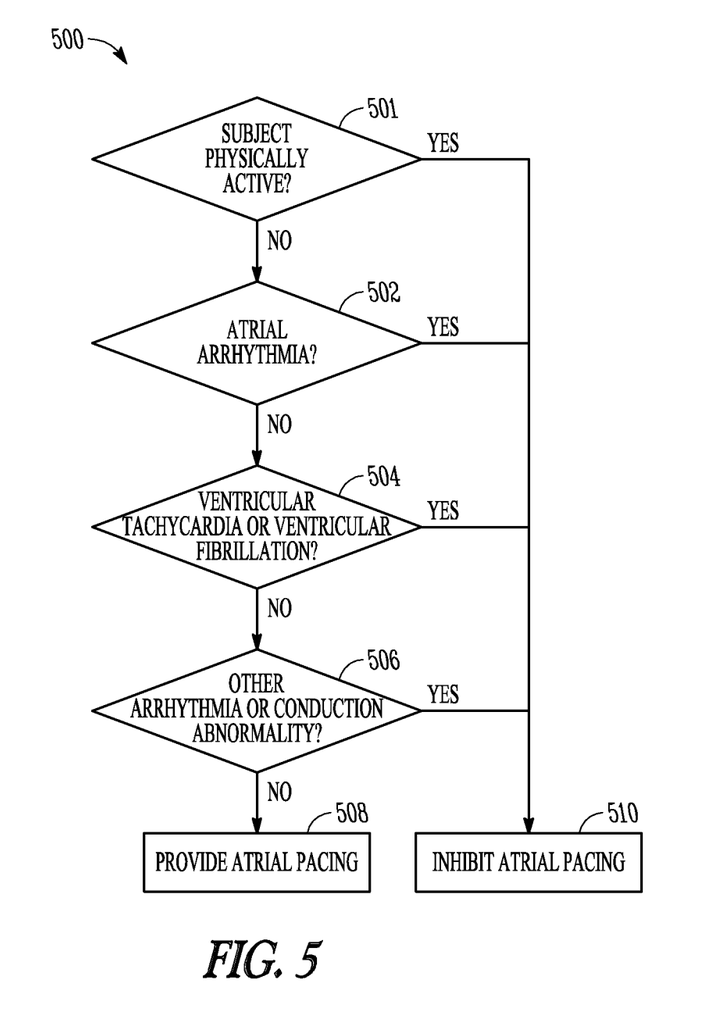
FIG. 5 is a chart illustrating an example of an algorithm for determining when to inhibit a method for determining an autonomic status indicator.

FIG. 5 is a flow chart illustrating an example of a method 500 for determining when to inhibit determining an autonomic status indicator, such as inhibiting method 300 or method 400, for determining an autonomic status indicator. The method 500 can be carried out by the CFM device 102, such as by executing or interpreting a sequence of instructions using the processor 204. At 501, an accelerometer 201 or any other sensor of physical activity or exertion, contained within or coupled to the CFM device 102, can perform a first detection test to determine whether the subject is physically active or at rest. If, at 501, physical activity is detected, then at 510 atrial pacing, as part of a method to determine an autonomic status indicator, is inhibited. At 501, if no physical activity is detected (e.g. the subject is at rest), then the process flows to 502. At 502, the CFM device 102 can perform a second detection test to determine whether the subject has an atrial tachyarrhythmia, such as by comparing the atrial heart rate to an atrial tachyarrhythmia rate threshold, comparing a morphology of an atrial depolarization to a template, or the like, such as described in Hsu U.S. Pat. No. 6,449,503 entitled "CLASSIFICATION OF SUPRAVENTRICULAR AND VENTRICULAR CARDIAC RHYTHMS USING CROSS CHANNEL TIMING ALGORITHM," assigned to the assignee of the present patent application, the disclosure of which is incorporated herein by reference in its entirety. At 502, if an atrial tachyarrhythmia is detected, then at 510 determining an autonomic status indicator using AV delay measured in response to atrial pacing at rest, is inhibited. At 502, if no atrial arrhythmia is detected, then the process flows to 504. At 504, a third detection test is performed to determine whether or not the subject has a ventricular tachycardia or ventricular fibrillation, such as by using a rate or morphology tachyarrhythmia detection technique. If, at 504, a ventricular tachycardia or ventricular fibrillation is detected, then at 510 atrial pacing, as part of a method to determine an autonomic status indicator, is inhibited. Otherwise, the process flows to 506, where a fourth detection test is performed to determine whether or not the subject has another cardiac arrhythmia or conduction abnormality. If, at 506, an arrhythmia or conduction abnormality is detected, then at 510 atrial pacing, as part of a method to determine an autonomic status indicator, is inhibited. Otherwise, at 508, atrial pacing, as part of a method to determine an autonomic status indicator, is provided. The method 500 can help ensure that only normal heart beats (not arrhythmic or ectopic beats) are used in measuring intrinsic AV delay. The method 500 can also help prevent the autonomic indicator determination using AV delay measured in response to atrial pacing at rest from potentially complicating a subject's pre-existing cardiac condition.

Figure 6:
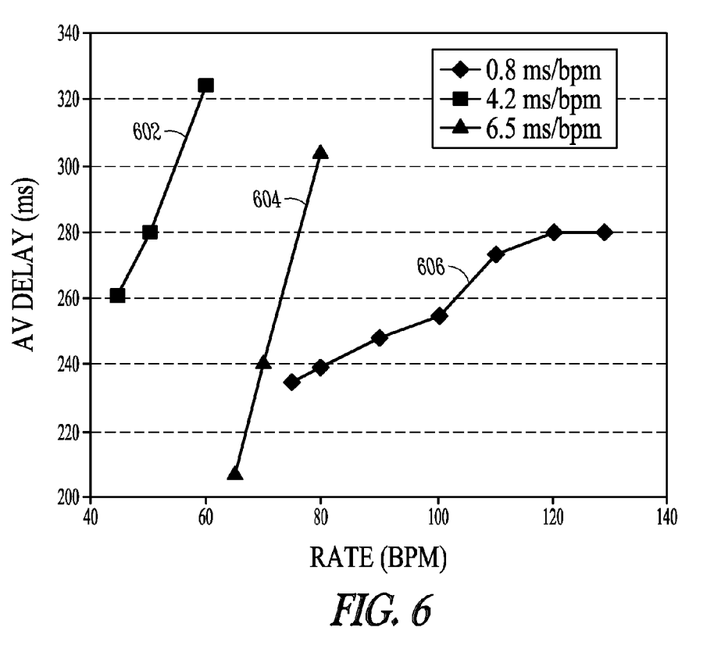
FIG. 6 is a graph of an example of atrial pacing rate versus median AV delay for three different subjects: a subject with moderate parasympathetic tone, a subject with decreased parasympathetic tone, and a subject with increased parasympathetic tone.

FIG. 6 is a graph of atrial pacing rate versus median AV delay for three different subjects: a subject with moderate parasympathetic tone, a subject with decreased parasympathetic tone, and a subject with increased parasympathetic tone. The graph illustrated in FIG. 6 can be obtained using method 300 described above with respect to FIG. 3. The Y-axis represents the median intrinsic AV delay in milliseconds (ms). The X-axis represents atrial pacing rate in beats per minute (bpm). Each data point represents a data pair including (1) a median intrinsic AV delay, and (2) the corresponding atrial pacing rate or interval at which the AV delays were measured.

Line 602 represents the slope (4.2 ms/bpm) for data pairs obtained from a subject with moderate parasympathetic tone. As can be seen from the slope of line 602, as the atrial pacing rate increases, the AV delays increase as well. This is a normal response for a subject with moderate parasympathetic tone who is undergoing atrial pacing at rest. As the atrial pace increases, the subject's parasympathetic nervous system causes the AV delay to lengthen in order to counteract the artificial increase in heart rate without a corresponding increase in metabolic demand.

Line 604 represents the slope for data pairs obtained from a subject with increased parasympathetic tone. Compared to the slope of line 602 (4.2 ms/bpm) illustrating a subject with moderate parasympathetic tone, the slope of line 604 (6.5 ms/bpm) is increased. It is believed that this is due to the subject's increased parasympathetic tone. As the atrial pacing rate is increased, the subject's AV delay increases more than would normally be expected because the subject's parasympathetic response is exaggerated. This subject may be too heavily medicated with beta-blockers or AV nodal blocking drugs, and this subject will likely demonstrate intolerance to physical activity. In order to treat this subject's autonomic imbalance, a physician might adjust the dosage of the subject's drug therapy. In order to properly titrate the dosage, can use method 300 or method 400 described above. Additionally, a physician might treat a subject with increased parasympathetic tone by optimizing the parameters of the subject's CFM device 102—such as by adjusting the AV delay, adjusting the lower rate pacing limit, or adjusting other settings of the device 102—in order to compensate for the subject's increased parasympathetic tone.

Line 606 represents the slope for data pairs obtained from a subject with decreased parasympathetic tone. Compared to the slope of line 602 (4.2 ms/bpm) illustrating a subject with moderate parasympathetic tone, the slope of line 606 (0.8 ms/bpm) is decreased. It is believed that this is due to the subject's decreased parasympathetic tone. As the atrial pacing rate is increased, the subject's AV delay does not increase as much as would normally be expected because the subject's parasympathetic response is blunted. In order to treat this subject's autonomic imbalance, a physician might use cardiac resynchronization therapy or drug therapy, including beta-blockers. An example of using cardiac resynchronization therapy includes optimizing the parameters of the subject's CFM device 102—such as by adjusting the AV delay, adjusting the lower rate pacing limit, or adjusting other settings of the device 102—in order to compensate for the subject's decreased parasympathetic tone.

Figure 7:
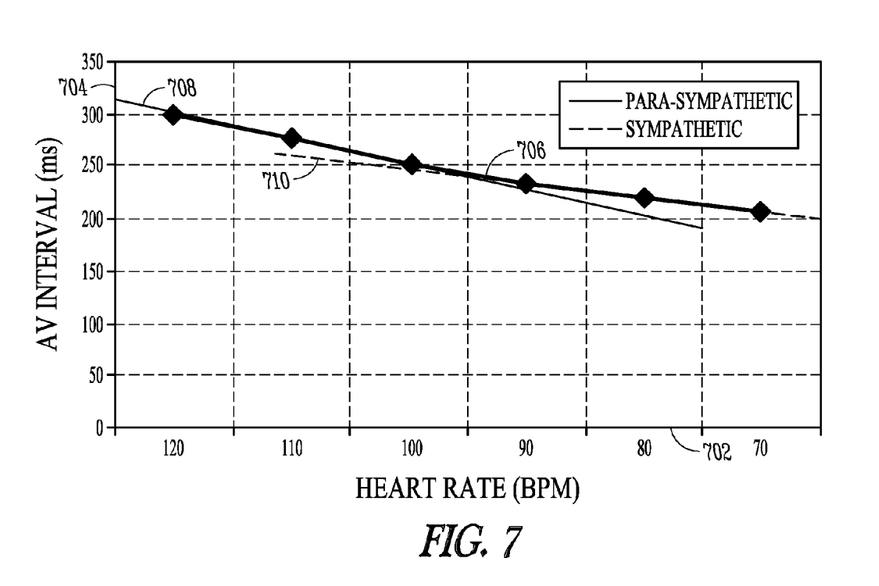
FIG. 7 is a graph of an example of hypothetical data illustrating the recovery rate of a subject's AV interval after atrial pacing has been discontinued.

Returning to method 400 illustrated in FIG. 4, the sequential measurements of the subject's intrinsic AV delay, performed by the CFM device after atrial pacing is discontinued at 408, can be plotted as a line on a x,y-graph, as shown using hypothetical data in FIG. 7. In FIG. 7, the x-axis 702 can represent heart rate, and the y-axis 704 can represent intrinsic AV interval. The overall slope of the line 706 (e.g., the change in intrinsic AV interval divided by the change in heart rate), can be representative of the rate of recovery during the recovery period duration. It is believed that changes in the slope of the line during the earlier phase of recovery 708 are due to the parasympathetic response, whereas changes in the slope of the line during the later phase of recovery 710 are due to the sympathetic response.

In an example, method 400 can be repeated over time, and the resulting slopes of the x,y-plots of heart rate versus intrinsic AV delay, representative of the rate of recovery, the can be trended over time. Such trends can be indicative of heart failure status and can signal impending heart failure decompensation. For example, sudden changes in the slope can suggest changes in the subject's sympathetic-parasympathetic balance, which can be indicative of worsening heart failure. In addition, the trended recovery rates can be used to assess intrinsic conduction changes over time, as well as to assess impending heart block. For example, if the slope of intrinsic AV delay versus heart rate gets shallower over time, indicating a slower recovery response, this could indicate AV nodal dysfunction and impending heart block.

In an example, an alert or alarm can be generated in response to changes in trended recovery rates that are indicative of heart failure decompensation or impending heart block. For example, changes in the trended recovery rates can be assessed periodically (e.g., weekly), and if the change is greater than a specified percentage (e.g., 20%), an alert can be generated via the Boston Scientific Corp. (Cardiac Pacemakers, Inc.) LATITUDE® Patient Monitoring System, which can automatically collect information from CFM device 102 and communicate the information to a another one of the subject's implanted or ambulatory personal medical device, such as via a local external interface 106 that can be communicatively coupled via a communication network 110 to a secure remote interface 108.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
  a cardiac rhythm management device, the cardiac rhythm management device comprising:
    an atrial pacing circuit, configured to provide, during a testing time period, atrial pacing to a subject at rest, over a specified range of atrial pacing rates or intervals; and
    an intrinsic AV delay measurement circuit, configured to:
      measure, during the testing time period, intrinsic AV delays of the subject, over the specified range of atrial pacing rates or intervals;
      determine a baseline intrinsic AV delay of the subject at rest during a time other than the testing time period; and
      in response to and after the atrial pacing is terminated, measure intrinsic AV delays of the subject during a recovery time period;
      determine a duration of the recovery time period based on the measured intrinsic AV delays; and
  a processor, included in or coupled to the cardiac rhythm management device, the processor configured to use information about the duration of the recovery time period of the intrinsic AV delay to determine a first autonomic status indicator representative of a sympathetic/parasympathetic balance of the subject.

2. The system of claim 1, wherein the processor is configured to use information about a relationship between (1) the measured intrinsic AV delays and (2) the provided atrial pacing rates or intervals, to determine a second autonomic status indicator representative of a sympathetic/parasympathetic balance of the subject; and
  wherein a user interface is configured to provide information about the second autonomic status indicator to a user or automated process.

3. The system of claim 2, wherein the processor is configured to:
  form data pairs, each data pair representing (1) the measured intrinsic AV delay and (2) corresponding atrial pacing rate or interval at which the AV delay was measured;
  define the relationship between (1) the measured intrinsic AV delays and (2) the provided atrial pacing rates or intervals using the data pairs;
  determine a slope or rate of change characteristic of the relationship; and
  use information about the slope or rate of change characteristic for providing the second autonomic status indicator representative of a sympathetic/parasympathetic balance of the subject.

4. The system of claim 3, wherein the processor is configured to compare the slope or rate of change characteristic of the relationship to a threshold value and use a result of the comparison for providing the second autonomic status indicator representative of a sympathetic/parasympathetic balance of the subject.

5. The system of claim 3, wherein the processor is configured to determine, for a data pair, a central tendency of multiple measured intrinsic AV delays associated with the same corresponding atrial pacing rate or interval.

6. The system of claim 2, wherein the processor is configured to combine information about the first and second autonomic status indicators; and
  wherein the user interface is configured to provide information about both the first and second autonomic status indicators to the user or automated process.

7. The system of claim 2, wherein the processor is configured to use the first and second autonomic status indicators to adjust a therapy provided to the subject by the cardiac rhythm management device.

8. The system of claim 1, wherein the recovery time period ends when the subject's measured AV delay is approximately equal to the baseline intrinsic AV delay.

9. The system of claim 1, wherein the cardiac rhythm management device is configured to provide atrial pacing, during the testing time period, at a rate that is above the subject's intrinsic resting heart rate.

10. The system of claim 1, comprising a user interface, coupled to the processor to receive information about the first autonomic status indicator, and to provide information about the first autonomic status indicator to a user or automated process.

11. The system of claim 1, wherein the processor is configured to use the first autonomic status indicator to adjust a therapy provided to the subject by a medical device.

12. The system of claim 11, wherein the therapy includes a neurostimulation therapy.

13. A method comprising:
  during a testing time period, using a cardiac rhythm management device for providing atrial pacing to a subject at rest, over a specified range of atrial pacing rates or intervals;

during the testing time period, using the cardiac rhythm management device for measuring intrinsic AV delays of the subject, over the specified range of atrial pacing rates or intervals;

determining a baseline intrinsic AV delay of the subject at rest during a time other than the testing time period;

in response to and after the atrial pacing is terminated, using the cardiac rhythm management device for measuring intrinsic AV delays of the subject during a recovery time period;

determining a duration of the recovery time period based on the measured intrinsic AV delays;

using information about the duration of the recovery time period of the intrinsic AV delay to determine, using a processor, a first autonomic status indicator representative of a sympathetic/parasympathetic balance of the subject; and providing information about the first autonomic status indicator to the user or automated process.

14. The method of claim 13, comprising:

using information about a relationship between (1) the measured intrinsic AV delays and (2) the provided atrial pacing rates or intervals, to determine, using a processor, a second autonomic status indicator representative of a sympathetic/parasympathetic balance of the subject; and providing information about the second autonomic status indicator to a user or automated process.

15. The method of claim 14, comprising:

forming data pairs, each data pair representing (1) the measured intrinsic AV delay and (2) corresponding atrial pacing rate or interval at which the AV delay was measured;

defining the relationship between (1) the measured intrinsic AV delays and (2) the provided atrial pacing rates or intervals using the data pairs;

determining a slope or rate of change characteristic of the relationship; and using information about the slope or rate of change characteristic for providing the second autonomic status indicator representative of a sympathetic/parasympathetic balance of the subject.

16. The method of claim 14, comprising combining information about the first and second autonomic status indicators, and comprising providing information about both the first and second autonomic status indicators to the user or automated process.

17. The method of claim 14, comprising using the first and second autonomic status indicators to adjust a therapy provided to the subject by a medical device.

18. The method of claim 13, wherein the recovery time period ends when the subject's measured AV delay is approximately equal to the baseline intrinsic AV delay.

19. The method of claim 13, wherein using the cardiac rhythm management device for providing atrial pacing includes providing atrial pacing at a rate that is above the subject's intrinsic resting heart rate.

20. The method of claim 13, wherein providing the first autonomic status indicator to a user or automated process includes using the first autonomic status indicator to adjust a therapy provided to the subject by the cardiac rhythm management device.

* * * * *